United States Patent
Ivancev et al.

(10) Patent No.: US 9,211,183 B2
(45) Date of Patent: Dec. 15, 2015

(54) THORACIC STENT GRAFT WITH GUIDE ARRANGEMENT

(75) Inventors: Krasnodar Ivancev, London (GB); Michael Lawrence-Brown, City Beach (AU); David Ernest Hartley, Wannanup (AU); Werner Dieter Ducke, Greenwood (AU); Roy K. Greenberg, Bratenahl, OH (US)

(73) Assignees: COOK MEDICAL TECHNOLOGIES LLC, Bloomington, IN (US); THE CLEVELAND CLINIC FOUNDATION, Cleveland, OH (US)

(*) Notice: Subject to any disclaimer, the term of this patent is extended or adjusted under 35 U.S.C. 154(b) by 731 days.

(21) Appl. No.: 13/498,492

(22) PCT Filed: Oct. 4, 2010

(86) PCT No.: PCT/US2010/051304
§ 371 (c)(1),
(2), (4) Date: Apr. 13, 2012

(87) PCT Pub. No.: WO2011/041773
PCT Pub. Date: Apr. 7, 2011

(65) Prior Publication Data
US 2012/0197383 A1  Aug. 2, 2012

Related U.S. Application Data

(60) Provisional application No. 61/278,203, filed on Oct. 2, 2009.

(51) Int. Cl.
*A61F 2/07* (2013.01)
*A61F 2/954* (2013.01)
(Continued)

(52) U.S. Cl.
CPC ... *A61F 2/07* (2013.01); *A61F 2/89* (2013.01); *A61F 2/954* (2013.01);
(Continued)

(58) Field of Classification Search
USPC ....................... 623/1.13, 1.16, 1.35
See application file for complete search history.

(56) References Cited

U.S. PATENT DOCUMENTS 5,683,449 A * 11/1997 Marcade ................. 128/898
2005/0004654 A1 * 1/2005 Khosravi et al. .......... 623/1.13
(Continued)

FOREIGN PATENT DOCUMENTS

EP 1847237 10/2007
WO WO99/13808 3/1999

OTHER PUBLICATIONS

Response to Examination Report for EPO 10 766 186.0 dated Apr. 22, 2014, 20 pgs.
(Continued)

*Primary Examiner* — Yashita Sharma
*Assistant Examiner* — Rebecca Preston
(74) *Attorney, Agent, or Firm* — Brinks Gilson & Lione

(57) ABSTRACT

A stent graft (1) has at least one fenestration (13) or low profile side arm (34). A guide assembly (17) surrounds the fenestration or low profile side arm. The guide assembly has a continuous wall extending laterally away from the outer surface of the stent graft. The continuous wall is substantially elliptical or circular and extends distally of the fenestration at a distal end of the wall and being coincident with a proximal part (25) of the periphery of the fenestration or low profile side arm at a proximal end of the wall (23). The wall acts to define a guide area to guide a flexible probe extended from a side branch vessel to enter the fenestration or low profile side arm. Where there are two fenestrations or low profile side arms there can be a single continuous wall (50) around both or separate walls for each. The wall may have a peripheral wire reinforcement (19).

14 Claims, 2 Drawing Sheets

(51) Int. Cl.
*A61F 2/06* (2013.01)
*A61F 2/89* (2013.01)

(52) U.S. Cl.
CPC .... *A61F 2002/061* (2013.01); *A61F 2002/075* (2013.01); *A61F 2210/0014* (2013.01); *A61F 2230/0006* (2013.01); *A61F 2230/0008* (2013.01)

(56) References Cited

U.S. PATENT DOCUMENTS

2006/0136046 A1* 6/2006 Hartley et al. ............... 623/1.35
2009/0030502 A1 1/2009 Sun et al.
2009/0216315 A1* 8/2009 Schreck et al. ............. 623/1.35

OTHER PUBLICATIONS

Examination Report for EPO 10 766 186.0 dated Nov. 20, 2013, 4 pgs.
International Search Report and Written Opinion for PCT/US2010/051304 dated Dec. 27, 2010, 11 pgs.
International Preliminary Report on Patentability for PCT/US2010/051304 dated Apr. 3, 2012, 7 pgs.
Patent Examination Report No. 1 for Australian Patent Application No. 2010300295 dated Feb. 6, 2013, 2 pgs.
Response to Patent Examination Report No. 1 for Australian Patent Application No. 2010300295 filed Apr. 9, 2013, 2 pgs.

* cited by examiner

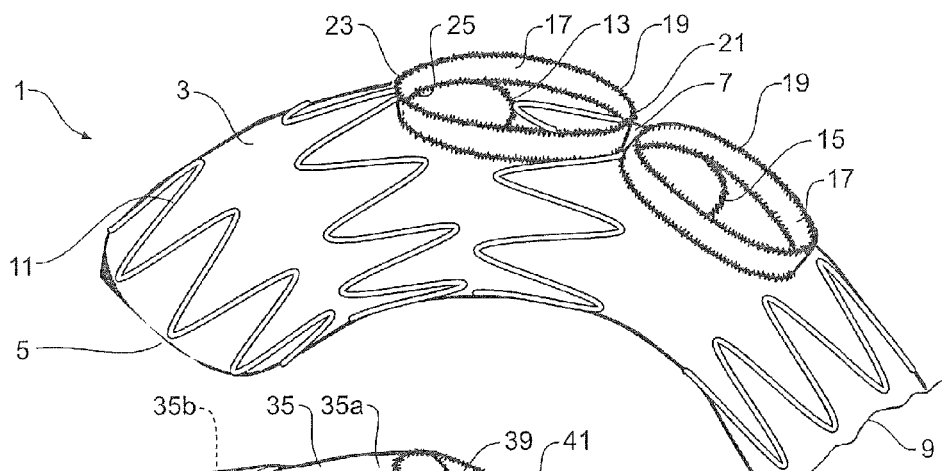
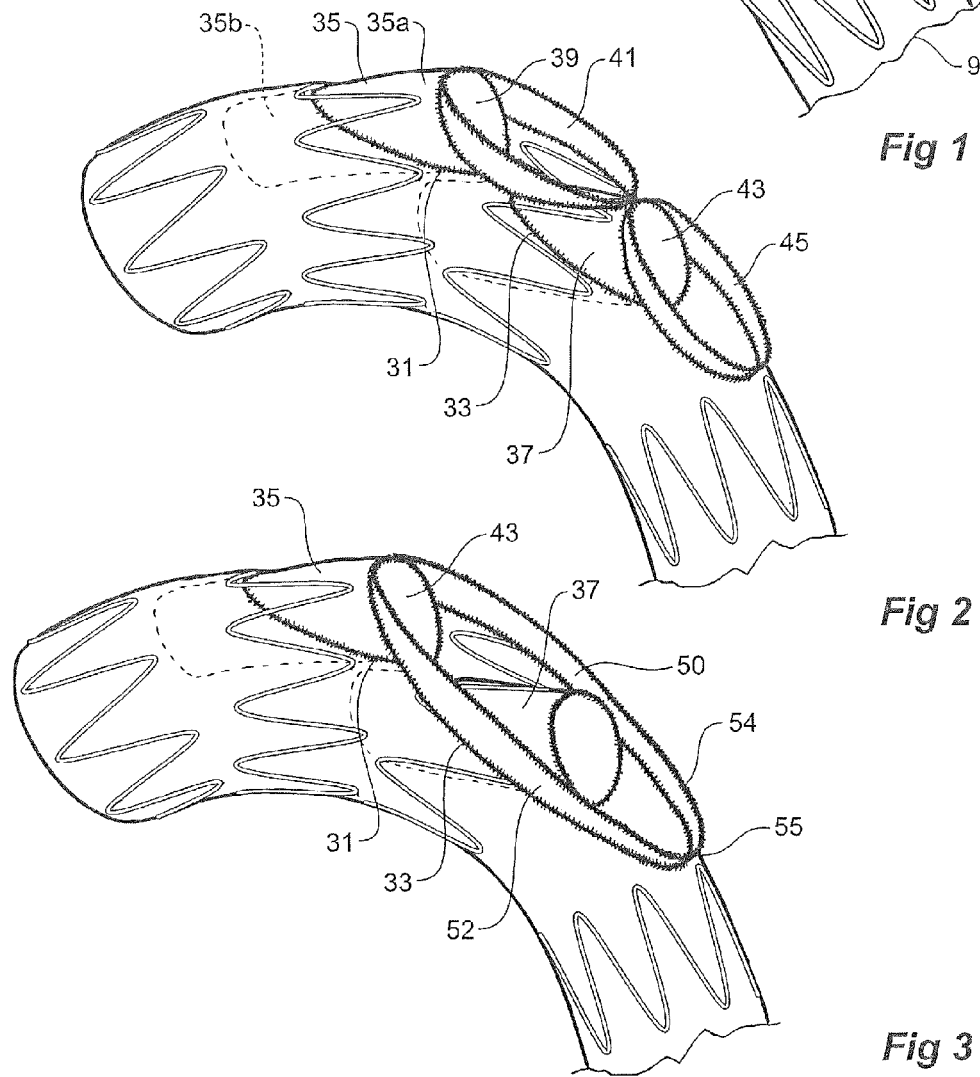
Fig 1
Fig 2
Fig 3

THORACIC STENT GRAFT WITH GUIDE ARRANGEMENT

RELATED APPLICATIONS

The present patent document is a §371 filing based on PCT Application Serial No. PCT/US2010/051304, filed Oct. 4, 2010 (and published as WO 2011/041773 A1 on Apr. 7, 2011), designating the United States and published in English, which claims the benefit of the filing date under 35 U.S.C. §119(e) of Provisional U.S. Patent Application Ser. No. 61/278,203, filed Oct. 2, 2009. All of the foregoing applications are hereby incorporated by reference in their entirety.

TECHNICAL FIELD

This invention relates to a medical device and more particularly to a stent graft deployed by endovascular techniques. More particularly it relates to a medical device for treatment of aortic arch disease.

BACKGROUND ART

In recent years endovascular implantable devices have been developed for treatment of aortic aneurysm. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system. The delivery system is inserted into the vascular system of the patient such as through a femoral incision. The leading end of the delivery system is maneuvered to the treatment site over a previously positioned guide wire. Through manipulation of a control system that extends to the proximal end of the catheter from the distal end of the system outside the patient the implantable device is then deployed by holding the device as its location and withdrawing a surrounding sheath. The stent graft or implantable device can then self expand or is expanded through the use of a balloon which is introduced with the stent graft introducible device. The stent graft becomes anchored into position to healthy wall tissue in the aorta such as by barbs after which the delivery system is removed leaving the device in position thereby bypassing an aneurysm in the aorta in a manner that channels all blood flow through the stent graft so that no blood flow enters the aneurysm, such that not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian and for treatment of an aneurysm in the region of the thoracic arch provision must be made for blood supply to continue to these arteries. For this purpose fenestrations or side branches are provided into a stent graft in that region. Access is generally obtained to these fenestrations to deploy side arms into the stent graft via the left or right brachial arteries or less commonly via the left or right carotid arteries. Once a guide wire has been introduced into the thoracic arch via such an artery the fenestration must be catheterized. To simplify this procedure it is desirable to have some working space between the stent graft and the wall of the aorta in the outer side of the thoracic arch. Owing to the nature of the arch, however, the stent graft will tend to engage against that outer wall.

The invention will be discussed in relation to a stent graft suitable for the thoracic arch of a patient but it is not so limited and may be applicable to any body cavities where access into a prosthetic device such as a stent graft is required from a side branch vessel.

It is the object of this invention to provide an arrangement of stent graft to overcome the above problem or to at least provide the practitioner with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DISCLOSURE OF THE INVENTION

In one form the invention is said to reside in a stent graft comprising an elongate tube of a biocompatible graft material and a plurality of stents therealong supporting the graft material, the elongate tube comprising a proximal end and a distal end and a inner surface and an outer surface, at least one fenestration in the elongate tube, the fenestration being defined by a periphery, and a guide assembly on the outer surface of the elongate tube, the guide assemble comprising a continuous wall extending laterally away from the outer surface of the elongate tube and surrounds the fenestration, the wall acting to define a guide area to guide a flexible probe extended from a side branch vessel to enter the fenestration.

Preferably the continuous wall is substantially elliptical or circular and extends distally of the fenestration at a distal end of the wall and being coincident with a proximal part of the periphery of the fenestration at a proximal end of the wall.

Preferably the continuous wall extends substantially radially away from the graft material tube.

Preferably the continuous wall comprises a biocompatible graft material.

Preferably the wall comprises a circumferential reinforcing wire at its outer edge whereby to assist in defining the guide area.

Preferably the stent graft comprises two fenestrations being a proximal and a distal fenestration and the fenestrations being substantially aligned longitudinally on the tubular body and a separate continuous wall around each fenestration, each continuous wall being substantially elliptical or circular and extending distally of the each fenestration respectively at a distal end of the wall and being coincident with a proximal part of the periphery of each fenestration at a proximal end of the wall and thereby defining two guide areas. Alternatively the continuous wall can be substantially elliptical and surround both the proximal and distal fenestrations and extend distally of the distal fenestration at a distal end of the wall and being coincident with a proximal part of the periphery of the proximal fenestration at a proximal end of the wall and thereby defining a single elongate guide area.

Preferably the or each fenestration comprises a low profile side arm, the low profile side arm comprising a graft material tube sealingly received into the fenestration wherein an inner portion of the graft material tube extends within the tubular body and an outer portion of the graft material tube extends exteriorly of the tubular body and such that the graft material tube extends from the tubular body at an angle thereto and the low profile side arm comprising an external open end facing distally.

In an alternate form the invention comprises a stent graft comprising an elongate tube of a biocompatible graft material and a plurality of stents therealong supporting the graft material, the elongate tube comprising a proximal end and a distal end and a inner surface and an outer surface, two fenestrations in the elongate tube, being a proximal and a distal fenestration in the tubular body, each fenestration being defined by a periphery, each fenestration comprising a low profile side arm, each low profile side arm comprising a graft material tube sealingly received into the respective fenestration wherein an inner portion of the graft material tube extends within the tubular body and an outer portion of the graft material tube extends exteriorly of the tubular body and such that the graft material tube extends from the tubular body at an angle thereto and the low profile side arm comprising an external open end facing distally, and a separate continuous wall extending laterally away from the outer surface of the elongate tube and surrounding each low profile side arm, each continuous wall being substantially elliptical or circular and extending distally of each low profile side arm respectively at a distal end of the wall and being coincident with a proximal part of the periphery of each low profile side arm at a proximal end of the wall and thereby defining two guide areas, the walls acting to define guide areas to guide a flexible probe extended from a side branch vessel to enter the low profile side arm.

In an alternate form the invention comprises a stent graft comprising an elongate tube of a biocompatible graft material and a plurality of stents therealong supporting the graft material, the elongate tube comprising a proximal end and a distal end and a inner surface and an outer surface, two fenestrations in the elongate tube, being a proximal and a distal fenestration in the tubular body, each fenestration being defined by a periphery, each fenestration comprising a low profile side arm, each low profile side arm comprising a graft material tube sealingly received into the respective fenestration wherein an inner portion of the graft material tube extends within the tubular body and an outer portion of the graft material tube extends exteriorly of the tubular body and such that the graft material tube extends from the tubular body at an angle thereto and the low profile side arm comprising an external open end facing distally and a guide assembly on the outer surface of the elongate tube, the guide assembly comprising a continuous wall extending laterally away from the outer surface of the elongate tube and wherein the continuous wall is substantially elliptical and surrounds both the proximal and distal low profile side arms and extends distally of the distal low profile side arm at a distal end of the wall and being coincident with a proximal part of the periphery of the proximal low profile side arm at a proximal end of the wall and thereby defining a single elongate guide area, the wall acting to define a guide area to guide a flexible probe extended from a side branch vessel to enter the low profile side arms.

Various stent types and stent constructions may be used in the stent-graft of the present invention. In general, the stents may be formed from any material and have any structure that is expandable and has sufficient radial strength to retain its shape. For example, the stents may be balloon expandable or self-expanding stents. The stents may be capable of radially contracting, radially distensible and/or deformable. Self-expanding stents include those that have a spring-like action which causes the stent to radially expand, or stents which expand due to the memory properties of the stent material for a particular configuration at a certain temperature. A preferred self-expanding stent is the Z-STENT®, available from Cook, Incorporated, Bloomington, Ind. USA.

Any suitable stent material is contemplated including, but not limited to, stainless steel, platinum, gold, titanium, nitinol and other nickel-titanium alloys, MP35N® and other nickel-cobalt alloys, Cobalt L-605™ and other cobalt-chromium alloys, other biocompatible metals, metal-alloys, as well as polymeric stents.

The stents may have the structure described in pending U.S. application Ser. No. 10/267,576, filed Oct. 8, 2002, which is hereby incorporated by reference, or U.S. Pat. Nos. 5,718,713, 5,741,327, 5,746,691, 5,843,175, 5,868,782, 6,042,606, 6,299,635 or co-pending U.S. Application Ser. No. 60/518,565, filed Nov. 8, 2003, each of which is hereby incorporated by reference.

BRIEF DESCRIPTION OF THE DRAWINGS

This then generally describes the invention but to assist with understanding reference will now be made to the accompanying drawings which show preferred embodiments of the invention.

In the drawings:

FIG. 1 shows detail of a portion of a stent graft incorporating a first embodiment of the present invention;

FIG. 2 shows detail of a portion of a stent graft incorporating a second embodiment of the present invention;

FIG. 3 shows detail of a portion of a stent graft incorporating a third embodiment of the present invention.

BEST MODE FOR CARRYING OUT THE INVENTION [OR MODE(S)/IF APPLICABLE]

Figure 4:
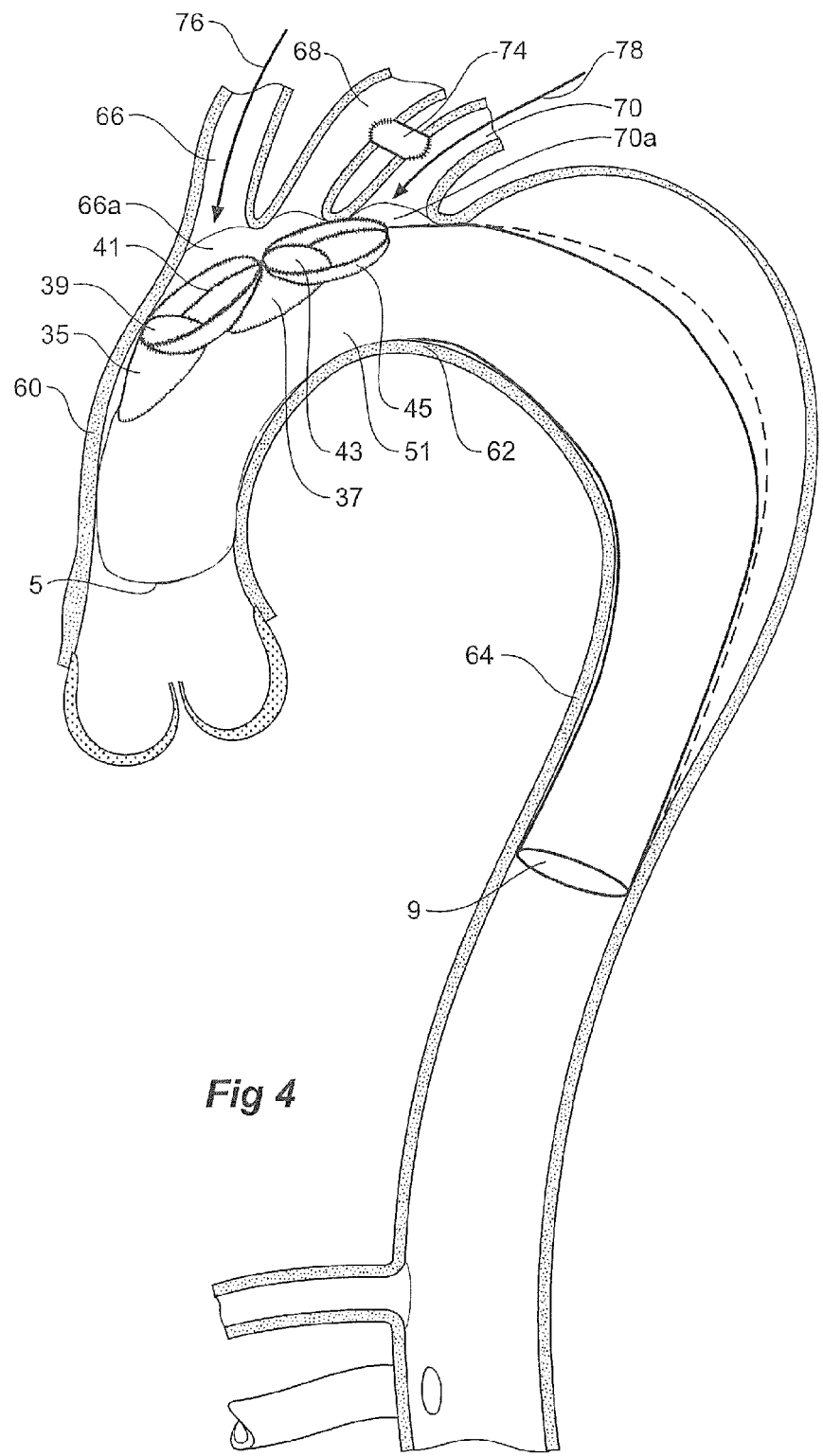
FIG. 4 shows a schematic view of a portion of the human aorta showing how the stent graft as depicted in FIG. 2 can be deployed into the aorta.

In FIG. 1 the stent graft 1 incorporating a first embodiment of the present invention comprises a tubular body 3 of a biocompatible graft material. Only a proximal portion of the tubular body 3 is shown. The full length of the stent graft may be from 10 to 20 cm long. The tubular body is shown in a longitudinally curved configuration. This may be achieved by tailoring the tubular body to a curved shape or it may be a cylindrical shape and which assumes a curved configuration when placed into the thoracic arch of a patient. The tubular body in the longitudinally curved configuration is adapted for placement into the thoracic arch of a patient with the proximal end 5 extending down the ascending aorta, the arched portion 7 in the thoracic arch and the distal end 9 in the descending aorta.

The tubular body 3 is supported by a plurality of self expanding stents 11. The stent graft has a proximal fenestration 13 and a distal fenestration 15 in its arched portion and substantially on the outside of the curved portion. The proximal fenestration 13 is for a side branch stent graft extending from the innominate or brachiocephalic artery and the distal fenestration 15 is intended usually for the left subclavian artery. In many situations a physician will provide a crossover graft between the left carotid artery and the left subclavian artery so that the distal fenestration 15 will serve the left carotid artery and the left subclavian artery.

Catheterization of each the proximal fenestration 13 and the distal fenestration 15 from the brachiocephalic artery and the left subclavian artery, respectively, can be difficult due the variations in relative position of each of these arteries both along the length of the thoracic arch and circumferentially around the thoracic arch and because of compound curvature of the thoracic arch. It is preferable to place the stent graft into the thoracic arch so that the proximal fenestration 13 and the distal fenestration 15 are slightly proximal of the expected positions of the arteries and then to have the guide assembly of the present invention provide the space and access needed for catheterization.

The guide assembly of this embodiment comprises a pair of continuous walls 17 extending laterally and radially away from the outer surface of the elongate tubular body 3 and surrounding each of the fenestrations. The wall acts to define a guide area to guide a flexible probe extended from one of the branch arteries to enter the fenestration.

The continuous wall 17 is substantially elliptical or circular and extends distally of the fenestration at a distal end 21 of the fenestration and is substantially coincident with a proximal part 23 of the periphery of the fenestration at a proximal end of the wall 25. The continuous wall would normally comprise a similar biocompatible graft material to that of the tubular body. To assist with maintaining the shape of the guide assembly the wall has a reinforcing wire 19 extending circumferentially at its outer edge. In this embodiment there are two separate guide assemblies, one around each fenestration.

When the stent graft is deployed into the thoracic arch the reinforcing wire 19 at the outer edge of the guide assembly will tend to engage against the outer side of the curve of the thoracic arch and the guide assembly will hold the stent graft slightly away from the outer side of the curve and define an access space into which a probe with a flexible tip can be inserted from a branch vessel and moved about until it enters the fenestration. Without the space provided by the guide assembly, with a slight misalignment catheterization would be extremely difficult or impossible.

FIG. 2 shows detail of a portion of a stent graft incorporating a second embodiment of the present invention. In this embodiment those items corresponding with those in FIG. 1 have the same reference numerals.

In FIG. 2 the fenestrations 31 and 33 have low profile side arms 35 and 37 fitted into them. Part of the low profile side arm 35a extends outside the fenestration 31 and part of the low profile side arm 35b extends inside the fenestration 31. The low profile side arm 35 has an external opening 39. The wall 41 of the guide arrangement extends from and around the external opening 39 and extends distally in a substantially elliptical shape.

The fenestration 33 has a low profile side arm 37 fitted into it and an external opening 43. The guide assembly 45 has a wall which extends from and around the external opening 43 and extends distally in a substantially elliptical shape.

FIG. 3 shows detail of a portion of a stent graft incorporating a third embodiment of the present invention. In this embodiment those items corresponding with those in FIG. 1 and FIG. 2 have the same reference numerals.

In FIG. 3 the fenestrations 31 and 33 have low profile side arms 35 and 37 fitted into them. In this case, however the guide assembly 50 includes a wall 52 which extends from and around the external opening 43 of the low profile side arm 35 and around the low profile side arm 37 and further distally to a distal end 55 in a substantially elliptical shape. Hence in this embodiment the guide assembly encompasses both fenestrations and their respective low profile side arms. To assist with maintaining the shape of the guide assembly the wall 52 has a reinforcing wire 54 extending circumferentially at its outer edge.

FIG. 4 shows a schematic view of a portion of the human aorta showing how the stent graft as depicted in FIG. 2 can be deployed into the aorta.

The thoracic arch shown schematically comprises an ascending aorta 60 extending to the thoracic arch 62 and a descending aorta 64 from the thoracic arch. Substantially at the top of the thoracic arch but slightly to the ventral side of the arch the major vessels branch off the arch. The major vessels are the brachiocephalic artery 66, the common carotid artery 68 and the left subclavian 70. In a preparatory operation an anastomosis 74 is provided between the common or left carotid artery 68 and the left subclavian 70. The anastomosis provides access between the common carotid artery 68 and the left subclavian artery 70 which enables endovascular access to the stent graft via brachial arteries the left arm rather than endovascular access via the left carotid artery which may be more complex.

The stent graft 1 is deployed into the thoracic arch by known techniques. The proximal end 5 of the stent graft 1 extends down the ascending aorta 60. The distal end of the stent graft 9 extends down the descending aorta 64. The stent graft 1 is deployed in the thoracic arch 62 so that the external opening 39 of the low profile side arm 35 is just proximal of the opening 66a of the brachiocephalic artery 66 into the thoracic arch and the guide assembly 41 extends distally to substantially the distal end of the opening 66a. Similarly the external opening 43 of the low profile side arm 37 is just proximal of the opening 70a of the left subclavian artery 70 into the thoracic arch and the guide assembly 45 extends distally towards the distal end of the opening 70a. A flexible guide wire extended as shown by the arrow 76 from the brachiocephalic artery 66 would have a good chance of being received in the guide arrangement 41 and be directed into the external opening 39 of the low profile side arm 35 thereby facilitating catheterization. Similarly a flexible guide wire extended as shown by the arrow 78 from the left subclavian artery 70 would have a good chance of being received in the guide arrangement 41 and be directed into the external opening 43 of the low profile side arm 37 thereby facilitating catheterization.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft comprising an elongate tube of a biocompatible graft material and a plurality of stents therealong supporting the graft material, the elongate tube comprising a proximal end and a distal end and an inner surface and an outer surface, at least one fenestration in the elongate tube, the at least one fenestration being defined by a periphery, and a guide assembly on the outer surface of the elongate tube, the guide assembly comprising a continuous wall extending laterally away from the outer surface of the elongate tube and surrounding the at least one fenestration, the wall defining a guide area to guide a flexible probe extended from a side branch vessel to enter the at least one fenestration, wherein the continuous wall is substantially elliptical or circular and extends distally of the at least one fenestration at a distal end of the wall and being coincident with a proximal part of the periphery of the at least one fenestration at a proximal end of the wall;

wherein the continuous wall has a radial extension that is less than an axial length of the guide assembly.

2. A stent graft as in claim 1 wherein the continuous wall extends substantially radially away from the graft material.

3. A stent graft as in claim 1 wherein the continuous wall comprises a second biocompatible graft material.

4. A stent graft as in claim 1 wherein the wall comprises a circumferential reinforcing wire at its outer edge whereby to assist in defining the guide area.

5. A stent graft as in claim 1 wherein the at least one fenestration comprises two fenestrations being a proximal and a distal fenestration in the elongate tube, wherein the continuous wall is a first continuous wall around the proximal fenestration, and further comprising a second continuous wall around the distal fenestration.

6. A stent graft as in claim 1 wherein the at least one fenestration comprises two fenestrations being a proximal and a distal fenestration in the elongate tube and wherein the continuous wall is substantially elliptical and surrounds both the proximal and distal fenestrations and extends distally of the distal fenestration at the distal end of the wall and being coincident with a proximal part of the periphery of the proximal fenestration at the proximal end of the wall and thereby defining a single elongate guide area.

7. A stent graft as in claim 1 wherein the or each fenestration comprises a low profile side arm, each low profile side arm comprising a graft material tube sealingly received into one of the at least one fenestration wherein an inner portion of each graft material tube extends within the elongate tube and an outer portion of each graft material tube extends exteriorly of the elongate tube and such that each graft material tube extends from the elongate tube at an angle thereto and each low profile side arm comprising an external open end facing distally.

8. A stent graft comprising an elongate tube of a biocompatible graft material and a plurality of stents therealong supporting the graft material, the elongate tube comprising a proximal end and a distal end and an inner surface and an outer surface, two fenestrations in the elongate tube, being a proximal and a distal fenestration in the elongate tube, each fenestration being defined by a periphery, the proximal fenestration comprising a proximal low profile side arm and the distal fenestration comprising a distal low profile side arm, each low profile side arm comprising a graft material tube sealingly received into the respective fenestration wherein an inner portion of each graft material tube extends within the elongate tube and an outer portion of each graft material tube extends exteriorly of the elongate tube and such that each graft material tube extends from the elongate tube at an angle thereto and each low profile side arm comprising an external open end facing distally and a guide assembly on the outer surface of the elongate tube, the guide assembly comprising a continuous wall extending laterally away from the outer surface of the elongate tube and wherein the continuous wall is substantially elliptical and surrounds both the proximal and distal low profile side arms and extends distally of the distal low profile side arm at a distal end of the wall and being coincident with a proximal part of the periphery of the proximal low profile side arm at a proximal end of the wall and thereby defining a single elongate guide area, the wall acting to define a guide area to guide a flexible probe extended from a side branch vessel to enter the low profile side arms.

9. A stent graft as in claim 8 wherein the wall comprises a circumferential reinforcing wire at its outer edge whereby to assist in defining the guide area.

10. A stent graft comprising an elongate tube of a biocompatible graft material and a plurality of stents therealong supporting the graft material, the elongate tube comprising a proximal end and a distal end and an inner surface and an outer surface, at least one fenestration in the elongate tube, the at least one fenestration being defined by a periphery, and a guide assembly on the outer surface of the elongate tube, the guide assembly comprising a continuous wall extending laterally away from the outer surface of the elongate tube and surrounding the at least one fenestration, the wall defining a guide area to guide a flexible probe extended from a side branch vessel to enter the at least one fenestration,
wherein the at least one fenestration comprises two fenestrations being a proximal and a distal fenestration in the elongate tube and wherein the continuous wall is substantially elliptical and surrounds both the proximal and distal fenestrations and extends distally of the distal fenestration at a distal end of the wall and being coincident with a proximal part of the periphery of the proximal fenestration at a proximal end of the wall and thereby defining a single elongate guide area.

11. A stent graft as in claim 10 wherein the continuous wall extends substantially radially away from the graft material.

12. A stent graft as in claim 10 wherein the continuous wall comprises a second biocompatible graft material.

13. A stent graft as in claim 10 wherein the wall comprises a circumferential reinforcing wire at its outer edge whereby to assist in defining the guide area.

14. A stent graft comprising an elongate tube of a biocompatible graft material and a plurality of stents therealong supporting the graft material, the elongate tube comprising a proximal end and a distal end and an inner surface and an outer surface, at least one fenestration in the elongate tube, the at least one fenestration being defined by a periphery, and a guide assembly on the outer surface of the elongate tube, the guide assembly comprising a continuous wall extending laterally away from the outer surface of the elongate tube and surrounding the at least one fenestration, the wall defining a guide area to guide a flexible probe extended from a side branch vessel to enter the at least one fenestration,
wherein the continuous wall is substantially elliptical or circular and extends distally of the at least one fenestration at a distal end of the wall and being coincident with a proximal part of the periphery of the at least one fenestration at a proximal end of the wall,
wherein the continuous wall and each of the at least one fenestration has a central point, the central points are asymmetrically aligned relative to each other.

\* \* \* \* \*